United States Patent
Szudajski et al.

(10) Patent No.: US 10,031,148 B2
(45) Date of Patent: Jul. 24, 2018

(54) SYSTEM FOR HANDLING A CORE SAMPLE

(71) Applicant: GE Energy Oilfield Technology, Inc., Houston, TX (US)

(72) Inventors: Thomas G. Szudajski, Houston, TX (US); John C. Boot, Atlanta, GA (US)

(73) Assignee: GE ENERGY OILFIELD TECHNOLOGY, INC., Houston, TX (US)

( * ) Notice: Subject to any disclaimer, the term of this patent is extended or adjusted under 35 U.S.C. 154(b) by 0 days.

(21) Appl. No.: 14/587,417

(22) Filed: Dec. 31, 2014

(65) Prior Publication Data
US 2016/0187361 A1   Jun. 30, 2016

(51) Int. Cl.
| | | |
|---|---|---|
| *G01N 35/00* | (2006.01) | |
| *G01N 33/24* | (2006.01) | |
| *B25J 9/16* | (2006.01) | |
| *G01N 21/3581* | (2014.01) | |
| *G01N 21/359* | (2014.01) | |
| *G01N 21/65* | (2006.01) | |

(52) U.S. Cl.
CPC ...... *G01N 35/00732* (2013.01); *B25J 9/1679* (2013.01); *G01N 33/24* (2013.01); *G01N 21/359* (2013.01); *G01N 21/3581* (2013.01); *G01N 21/65* (2013.01); *G01N 35/0099* (2013.01); *G01N 2035/00851* (2013.01)

(58) Field of Classification Search
CPC .............. G01N 35/00732; G01N 33/24; E21B 47/0002
See application file for complete search history.

(56) References Cited

U.S. PATENT DOCUMENTS

| | | |
|---|---|---|
| 3,704,898 A | 12/1972 | Schmidt |
| 3,746,369 A | 7/1973 | Neff |
| 4,244,417 A | 1/1981 | Taylor |
| (Continued) | | |

FOREIGN PATENT DOCUMENTS

GB    2135049 A  *  8/1984  ............... G01V 5/00

OTHER PUBLICATIONS

Reddy, B., "An FFT-Based Technique for Translation, Rotation, and Scale-Invariant Image Registration," IEEE Transactions on Image Processing, vol. 5, No. 8, Aug. 1996, pp. 1266-1271.
(Continued)

*Primary Examiner* — Christine S Kim
(74) *Attorney, Agent, or Firm* — Hogan Lovells US LLP

(57) ABSTRACT

An automated system for handling core samples in and out of an imaging device retrieves the samples from a staging area. During handling, the identity of each core sample is known to the system so that the imaging results are correlated appropriately. The system positions the core sample so the vertical and slab side orientations of the core sample discernable during handling. Core samples are staged in a location, and the automated system includes a robotic arm, which senses the core sample to discern its vertical and slab slot orientations, and then loads the core sample into the imaging device. When imaging is complete, the automated system removes the core sample from the imaging device; and in designated circumstances, transfers the core sample to a location for further analysis. In one example the further analysis is based on analyzing areas of interest identified in the core sample.

20 Claims, 6 Drawing Sheets

(56) References Cited

U.S. PATENT DOCUMENTS

| | | |
|---|---|---|
| 4,571,491 A | 2/1986 | Vinegar et al. |
| 4,583,242 A | 4/1986 | Vinegar et al. |
| 4,616,134 A | 10/1986 | Pruett et al. |
| 4,909,557 A | 3/1990 | De Weck et al. |
| 4,924,187 A | 5/1990 | Sprunt et al. |
| 4,977,586 A | 12/1990 | Curry |
| 5,025,150 A | 6/1991 | Oldham et al. |
| 5,109,398 A | 4/1992 | Hunt et al. |
| 5,153,899 A | 10/1992 | Curry |
| 5,318,123 A | 6/1994 | Venditto et al. |
| 5,360,066 A | 11/1994 | Venditto et al. |
| 5,386,875 A | 2/1995 | Venditto et al. |
| 5,409,251 A | 4/1995 | Thorndyke |
| 5,509,687 A | 4/1996 | Thorndyke |
| 5,712,893 A * | 1/1998 | Dykster .............. G01N 23/04 378/205 |
| 5,947,213 A | 9/1999 | Angle et al. |
| 6,118,839 A | 9/2000 | Dafni et al. |
| 6,430,547 B1 | 8/2002 | Busche |
| 6,481,887 B1 | 11/2002 | Mirabella |
| 6,816,787 B2 | 11/2004 | Ramamoorthy |
| 6,940,941 B2 | 9/2005 | Gregerson et al. |
| 7,082,185 B2 | 7/2006 | Freifeld et al. |
| 7,113,569 B2 | 9/2006 | Okumura et al. |
| 7,172,038 B2 | 2/2007 | Terry et al. |
| 7,175,347 B2 | 2/2007 | Tybinkowski et al. |
| 7,564,944 B2 | 7/2009 | Kato |
| 7,714,304 B2 | 5/2010 | Poglitsch |
| 7,853,045 B2 | 12/2010 | Touati |
| 7,866,386 B2 | 1/2011 | Beer et al. |
| 8,068,579 B1 | 11/2011 | Yun et al. |
| 8,081,796 B2 | 12/2011 | Derzhi et al. |
| 8,081,802 B2 | 12/2011 | Dvorkin et al. |
| 8,085,974 B2 | 12/2011 | Dvorkin et al. |
| 8,155,377 B2 | 4/2012 | Dvorkin et al. |
| 8,170,799 B2 | 5/2012 | Dvorkin et al. |
| 8,234,912 B2 | 8/2012 | Suarez-Rivera et al. |
| 8,327,932 B2 | 12/2012 | Karanikas et al. |
| 8,331,626 B2 | 12/2012 | Wojcik et al. |
| 8,542,793 B1 | 9/2013 | Jin |
| 8,562,078 B2 | 10/2013 | Burns et al. |
| 8,590,382 B2 | 11/2013 | Zaleski, Jr. et al. |
| 8,636,323 B2 | 1/2014 | Prince-Wright et al. |
| 8,657,000 B2 | 2/2014 | Willingham et al. |
| 8,725,477 B2 | 5/2014 | Zhang et al. |
| 9,063,247 B2 | 6/2015 | Li et al. |
| 9,103,176 B2 | 8/2015 | Delmar et al. |
| 9,196,058 B2 | 11/2015 | Mezghani |
| 9,507,047 B1 | 11/2016 | Dvorkin et al. |
| 9,573,434 B2 | 2/2017 | Boot et al. |
| 2002/0018542 A1 | 2/2002 | Fenkart et al. |
| 2003/0107735 A1 | 6/2003 | Bland et al. |
| 2004/0218716 A1* | 11/2004 | Freifeld ................ G01N 23/04 378/62 |
| 2005/0127620 A1 | 6/2005 | Amundson |
| 2008/0217559 A1 | 9/2008 | Poglitsch et al. |
| 2009/0078467 A1 | 3/2009 | Castillo |
| 2009/0260415 A1* | 10/2009 | Suarez-Rivera ......... G01N 3/46 73/7 |
| 2010/0250139 A1 | 9/2010 | Hobbs et al. |
| 2010/0324868 A1* | 12/2010 | Russell ................ B23K 10/00 703/1 |
| 2011/0150177 A1 | 6/2011 | Groot |
| 2012/0136196 A1 | 5/2012 | Foxall et al. |
| 2012/0148398 A1 | 6/2012 | Campbell et al. |
| 2012/0230151 A1 | 9/2012 | Almaguer |
| 2013/0083888 A1 | 4/2013 | Jin |
| 2013/0170713 A1* | 7/2013 | Kumar ................ E21B 47/022 382/109 |
| 2013/0182819 A1 | 7/2013 | Dvorkin et al. |
| 2013/0301794 A1 | 11/2013 | Grader et al. |
| 2013/0308753 A1* | 11/2013 | Groves ................ E21B 49/06 378/54 |
| 2014/0086381 A1 | 3/2014 | Grader et al. |
| 2014/0119501 A1 | 5/2014 | O'Hare et al. |
| 2014/0327760 A1* | 11/2014 | Kurz .................... H04N 5/332 348/135 |
| 2014/0367086 A1 | 12/2014 | Arian et al. |
| 2015/0044004 A1 | 2/2015 | Pham et al. |
| 2015/0062300 A1* | 3/2015 | Li ........................ E21B 49/00 348/46 |
| 2015/0063650 A1* | 3/2015 | Hu ....................... E21B 49/00 382/109 |
| 2015/0176404 A1* | 6/2015 | Smith ................ G01N 23/222 73/152.11 |
| 2015/0177409 A1 | 6/2015 | Sofiienko |
| 2015/0185122 A1 | 7/2015 | Lakshtanov et al. |
| 2016/0131793 A1 | 5/2016 | Szudajski |

OTHER PUBLICATIONS

Wang, Qiang et al., "Automatic Registration of Remote Sensing Image with Moderate Resolution," College of Geoscience and Surveying Engineering, CUMT, Beijing, China; Apr. 24-26, 2012; pp. 404-409.

Renard et al., "3D imaging of fracture propagation using synchroton X-ray microtomography," Earth and Planetary Science Letters, 286, 2009, pp. 285-291.

* cited by examiner

SYSTEM FOR HANDLING A CORE SAMPLE

BACKGROUND OF THE INVENTION

1. Field of Invention

The present disclosure relates in general to a system for imaging a core sample from a wellbore. More specifically, the present disclosure relates to a system for maintaining orientation and identification of a core sample while analyzing the core sample.

2. Description of Prior Art

Various techniques are currently in use for identifying the presence of hydrocarbons in subterranean formations. Some techniques employ devices that emit a signal from a seismic source, and receive reflections of the signal on surface. Others involve disposing logging devices downhole in a wellbore intersecting the subterranean formation, and interrogating the formation from within the wellbore. Example downhole exploration devices include seismic tools that can transmit and receive seismic signals, or ones that simply receive a seismic signal generated at surface. Other devices collect and sample fluid from within the formation or from within the wellbore. Nuclear tools are also employed that direct radiation into the formation, and receive radiation that scatters from the formation. Analyzing the scattered radiation can provide information about fluids residing in the formation adjacent the wellbore, the type of fluid, and information about other materials next to the wellbore, such as gravel pack.

Logging downhole also is sometimes done while the wellbore itself is being drilled. The logging devices are usually either integral with a drill bit used during drilling, or on a drill string that rotates the drill bit. The logging devices typically are either nuclear, seismic, can in some instances optical devices. In some instances, a core is taken from the wellbore and analyzed after being retrieved to the surface. Analyzing the core generally provides information about the porosity and/or permeability of the rock formation adjacent the wellbore. Cores are generally elongated cylindrical members and obtained with a coring tool having an open barrel for receiving and retaining the core sample.

SUMMARY OF THE INVENTION

Disclosed herein is an example of an automated system for handling core samples in and out of an imaging device. An example of a method of analyzing a core sample includes providing information on the core sample, retrieving the information provided on the core sample, and handling the core sample based on the step of retrieving the information provided on the core sample. The core sample can optionally be imaged, and while being maintained in a designated orientation based on the information retrieved from the core sample. The information retrieved from the core sample may be correlated with an image obtained by imaging the core sample. The core sample may optionally be moved to a designated location based on information obtained from the step of imaging the core sample. This example may further include analyzing the core sample at the designated location with one or more of a spectroscope, a laser, and combinations thereof. In an alternative, the information provided on the core sample can be a core identifier, vertical orientation of the core sample, slab side orientation of the core sample, and combinations thereof. The step of handling the core sample can involve using a core handling system with an articulated arm to insert the core sample into a core sample imaging device. The method may also include disposing the core sample at a staging area, and wherein the step of handling the core sample includes moving the core sample from the staging area to the core sample imaging device with the core handling system.

In another example method of analyzing a core sample, information is provided on the core sample, the information provided on the core sample is retrieved, the core sample is handled based on the step of retrieving the information provided on the core sample, the core sample is imaged while being maintained in a designated orientation based on the information retrieved from the core sample, and the information retrieved from the core sample is correlated with an image obtained by imaging the core sample. The method may further involve moving the core sample to a designated location based on information obtained from the step of imaging the core sample. In an embodiment, handling the core sample involves using a core handling system with an articulated arm to insert the core sample into a core sample imaging device. The method can further include disposing the core sample at a staging area, and wherein the step of handling the core sample involves moving the core sample from the staging area to the core sample imaging device with the core handling system.

Also disclosed herein is an example of a system for analyzing a core sample and which includes a mobile enclosure, a core sample imaging device within the mobile enclosure, a loading assembly that selectively receives the core sample, and a core handling system that selectively handles the core sample between the loading assembly and a staging area. The core handling system may include an articulated arm for manipulating the core sample. Alternatively, the core handling system may include a scanner that scans information provided on the core sample to identify the core sample. In one embodiment the core handling system maintains the core sample in a designated orientation based on information provided on the core sample. Information about the core sample may be listed on identification tags provided on the core sample. In this example, the information is made up of data that includes a core identifier, vertical orientation of the core sample, slab side orientation of the core sample, and combinations thereof. A controller may be included that is in communication with the core sample imaging device and the core handling system.

BRIEF DESCRIPTION OF DRAWINGS

Some of the features and benefits of the present invention having been stated, others will become apparent as the description proceeds when taken in conjunctions with the accompanying drawings, in which.

Figure 1:
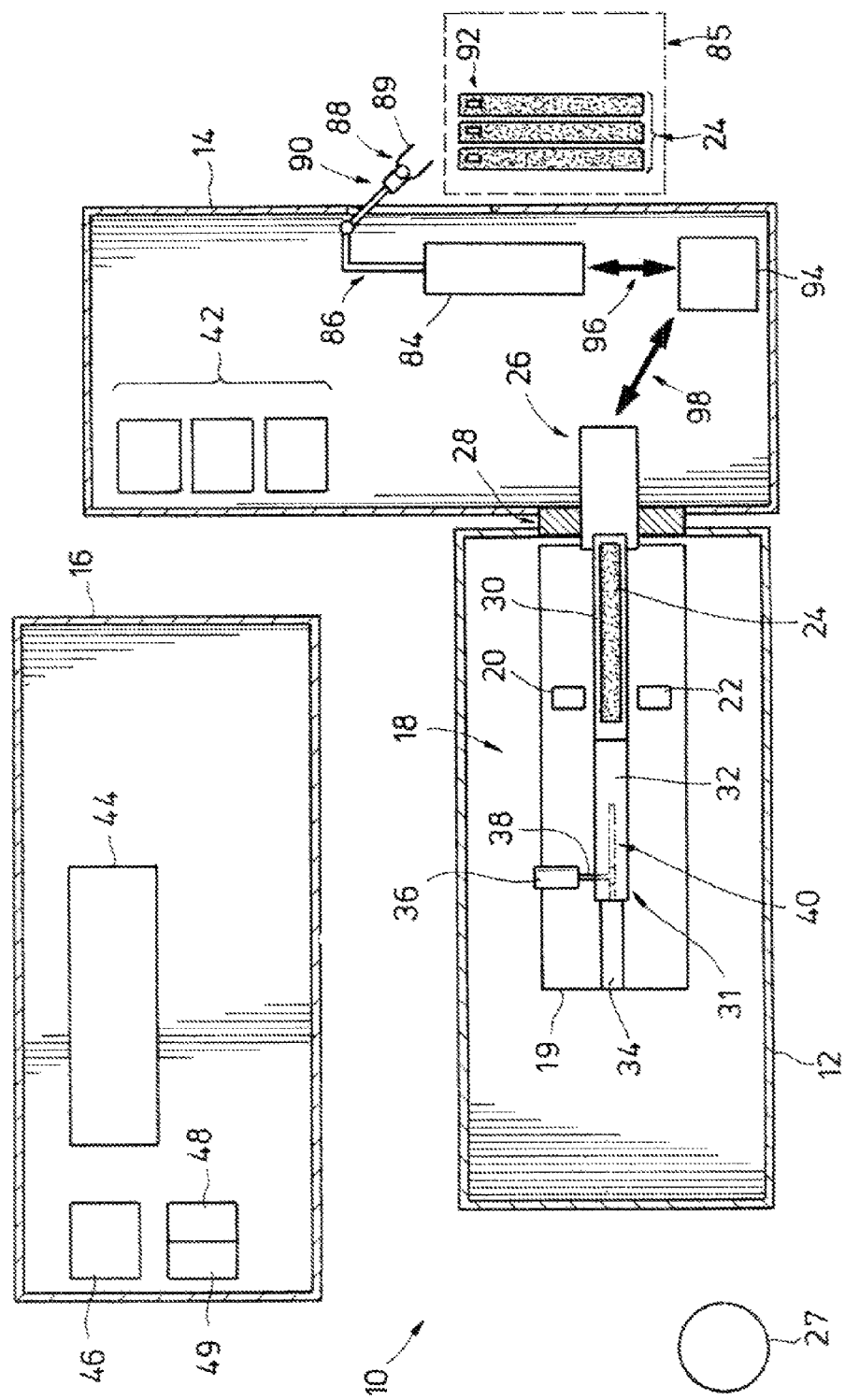
FIG. 1 is a plan partial sectional view of an example of a system for analyzing a core sample.

While the invention will be described in connection with the preferred embodiments, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF INVENTION

The method and system of the present disclosure will now be described more fully hereinafter with reference to the accompanying drawings in which embodiments are shown. The method and system of the present disclosure may be in many different forms and should not be construed as limited to the illustrated embodiments set forth herein; rather, these embodiments are provided so that this disclosure will be thorough and complete, and will fully convey its scope to those skilled in the art. Like numbers refer to like elements throughout. In an embodiment, usage of the term "about" includes, but is not necessarily limited to, +/−5% of the cited magnitude. In an embodiment, usage of the term "substantially" includes, but is not necessarily limited to, +/−5% of the cited magnitude.

It is to be further understood that the scope of the present disclosure is not limited, to the exact details of construction, operation, exact materials, or embodiments shown and described, as modifications and equivalents will be apparent to one skilled in the art. In the drawings and specification, there have been disclosed illustrative embodiments and, although specific terms are employed, they are used in a generic and descriptive sense only and not for the purpose of limitation.

Shown in a plan partial sectional view in FIG. 1 is one example of a core analysis system 10, which includes first, second and third mobile enclosures. In the example of FIG. 1, the first mobile enclosure is a scan trailer 12, the second mobile enclosure is a handling trailer 14, and the third mobile enclosure is an analysis trailer 16. In one example, each of the enclosures may be part of a tractor trailer and which are movable by a tractor trailer. Schematically illustrated in the scan trailer 12 is a scan system 18, and substantially all of which is housed within a cabinet 19. In the illustrated example, cabinet 19 is specially designed to shield any radiation within, generated, inherent, or otherwise, from making its way to outside of the cabinet 19. Thus, cabinet 19 is in compliance with 21 C.F.R. 1020.40. Further shown in cabinet 19 is a scan source 20, which in one embodiment includes a device for emitting radiation, such as but not limited to an X-ray, microwave, millimeter wave, etc. A scan receiver 22 is also shown provided within cabinet 19 and combined with scan source 20, in one example, forms a Computed Tomography (CT) scanner.

An elongate and cylindrical core sample 24 is shown axially inserted within scan system 18. Core sample 24 is disposed into scan system 18 through a loading assembly 26, which is shown coupled to one end of the scan system 18 and projecting through an opening in a side wall of handling trailer 14. In an example, core sample 24 is taken from a subterranean formation below system 10, and is retrieved via a wellbore 27 shown adjacent system 10. Thus the wellbore 27 intersects the subterranean formation. Embodiments exist where the system 10 is "onsite" in the field and where the distance between the wellbore 27 to system 10 can range from less than one hundred yards up to five miles, and any distance between. Accordingly, real time analysis while drilling the wellbore 27 can take place within the system 10. Feedback from the analysis can be used by the drilling operator to make adjustments or changes to the drilling operation.

A hatch assembly 28 is schematically illustrated which provides the coupling interface between trailers 12, 14 and includes sealing around the loading assembly 26. While in scan system 18, core sample 24 rests on a core carrier 30. In an example, core carrier 30 is fabricated from a material transparent to X-Rays, and can support the load of the core sample 24 with minimum deflection to maintain the resolution of a stationary scanner. Core carrier 30 is part of a manipulator system 31, which further includes a manipulator arm 32 that telescopingly moves along a manipulator base 34. As shown, an end of manipulator arm 32 distal from manipulator base 34 couples onto an end of core carrier 30, so that core carrier is basically cantilevered on an end of the manipulator arm 32. Manipulator arm 32 is shown in an extended position over manipulator base 34. Manipulator arm 32 axially moves with respect to manipulator base 34 via a motor 36 shown having a shaft 38 that couples to manipulator arm 32. In one example, motor 36 is a linear direct current motor. A gear (not shown) on an end of shaft 38 distal from motor 36 engages a gear rack 40 that is provided on manipulator arm 32. Accordingly, selectively operating motor 36 urges manipulator arm 32, core carrier 30 and core sample 24 in an axial direction with respect to scan source 20. Moving manipulator arm 32 into a retracted position onto manipulator base 34 positions the entire length of core sample 24 in scan system 18, so that all of core sample 24 may be analyzed by the scan system 18. In one example, the scan source 20 and scan receiver 22 orbit around the core sample 24 and so that when in combination of axial movement of core sample 24 within system 18, a helical scan is taken of core sample 24. Further optionally, motor 36, or additional motors not shown, may manipulate and selectively move manipulator arm vertically and/or laterally to thereby better position core sample 24 into a designated orientation and/or spatial position during the scanning process.

Further shown in FIG. 1 are a series of work surfaces 42 provided within handling trailer 14. In one example of operation, before or after core sample 24 is scanned, it may be broken into sections for further analysis and analyzed on surfaces 42. Examples of the surfaces 42 include a crusher, sample divider, and mortar grinder. Additional analysis may take place within analysis trailer 16. Schematically illustrated within analysis trailer 16 are a variety of analysis equipment such as, but not limited to, scanners and spectrometers. One such analysis equipment is a nanotom 44, which can include a scanning system for scanning the internals of core sample 24, or parts of the core sample. Further analysis equipment in the analysis trailer 16 may be a laser induced spectroscope 46, a Raman spectroscope 48, and near infrared spectroscope 49. It will be understood that alternate embodiments may include more trailers or fewer trailers. For example, an appropriately sized scan system 18 may allow loading assembly 26 to be in scan trailer 12 without projecting through an opening in the trailer and without a hatch assembly 28. A further embodiment may provide work surfaces 42 in the same trailer as the analysis equipment, or the analysis equipment may be contained in handling trailer 14. In yet a further embodiment, scan system 18, loading assembly 26, work surfaces 42 and analysis equipment (e.g., nanotom 44, spectroscopes 46, 48, 49, or others) are all contained in one trailer.

Figure 2:
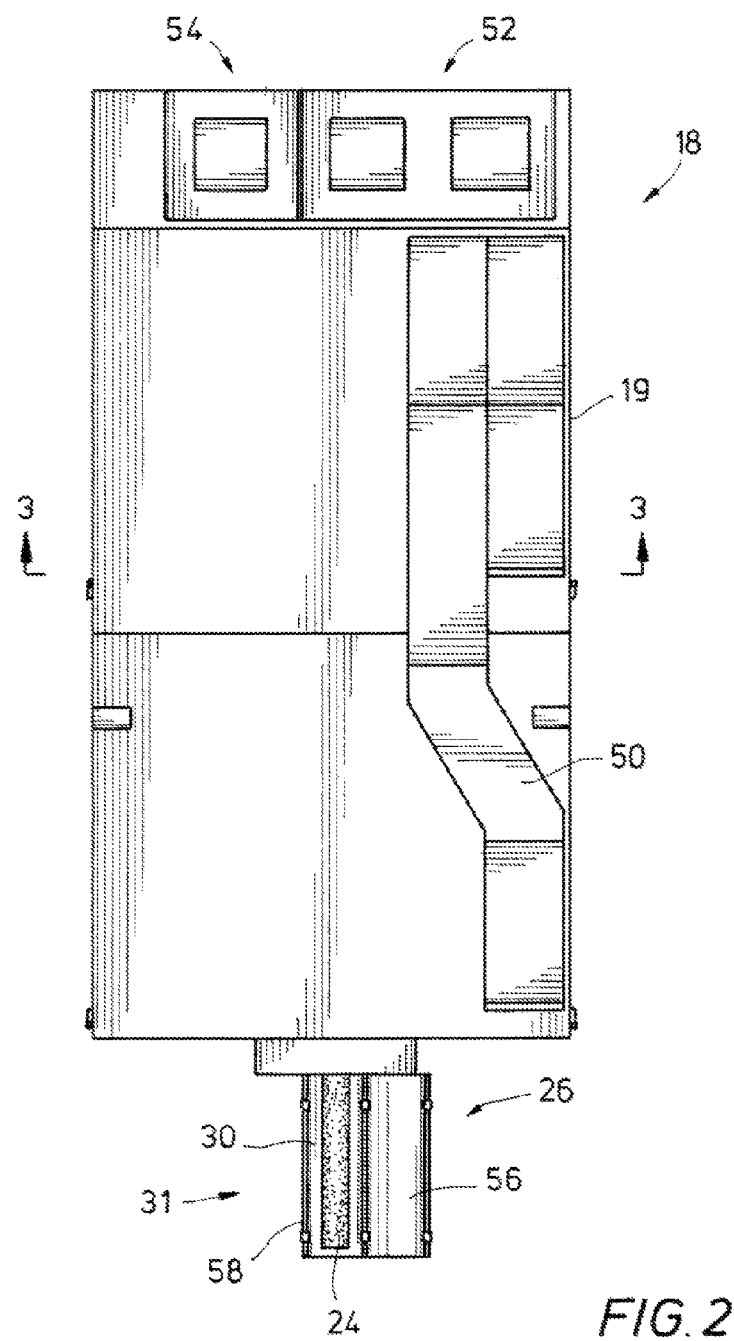
FIG. 2 is an overhead view of an example of a cabinet for shielding radiation and conditioning a scanning unit for a core sample.

Referring now to FIG. 2, shown in an overhead view is an example of the scan system 18 and an upper surface of cabinet 19. Further illustrated in this example is a conditioning vent 50 on an upper end of the cabinet 19, where conditioning vent 50 provides a path for airflow and that is used in conditioning the inside of the cabinet 19, while blocking the leakage of any radiation from cabinet 19. An advantage of the conditioning vent 50 is that conditioned air at proper temperature and humidity may be injected into the inside of cabinet 19 so that the sensitive devices housed within the cabinet 19 may be maintained in proper operating conditions to ensure normal operating functionality. In an example, operational conditions require maintaining a substantially constant temperature within the cabinet 19. In one embodiment, the temperature variation in the cabinet 19 is kept of within 2 degrees C. of a designated temperature. An advantage of the device described herein is that the temperature in the cabinet 19 can be maintained within the designated range in spite of substantial air replacement. Air replacement in the cabinet 19, due to the loading mechanism operation, maintains temperature uniformity across the scanner frame and rotary element. In one example, the volumetric rate of air replacement is at least about 4 $m^3$/min. A power distribution panel 52 is shown provided at an aft end of cabinet 19, and which includes buses (not shown) and other devices for distributing power through cabinet 19 into scan system 18. A control panel 54 is shown adjacent power distribution panel 52 and includes hardware and software for managing control of the operation of the systems house within cabinet 19. Projecting outward past the forward end of cabinet 19 is the loading assembly 26 in an open configuration. In the illustrated example, the loading assembly 26 includes a loading cover 56 and loading basin 58, where the loading cover 56 is shown swung open from a loading basin 58. As shown the core sample 24 has been inserted into open loading assembly 26 and onto the core carrier 30. As will be described in more detail below, safety features are included with the system that prevent operation of the manipulator system 31 when the loading assembly 26 is in the open position of FIG. 2.

Figure 3:
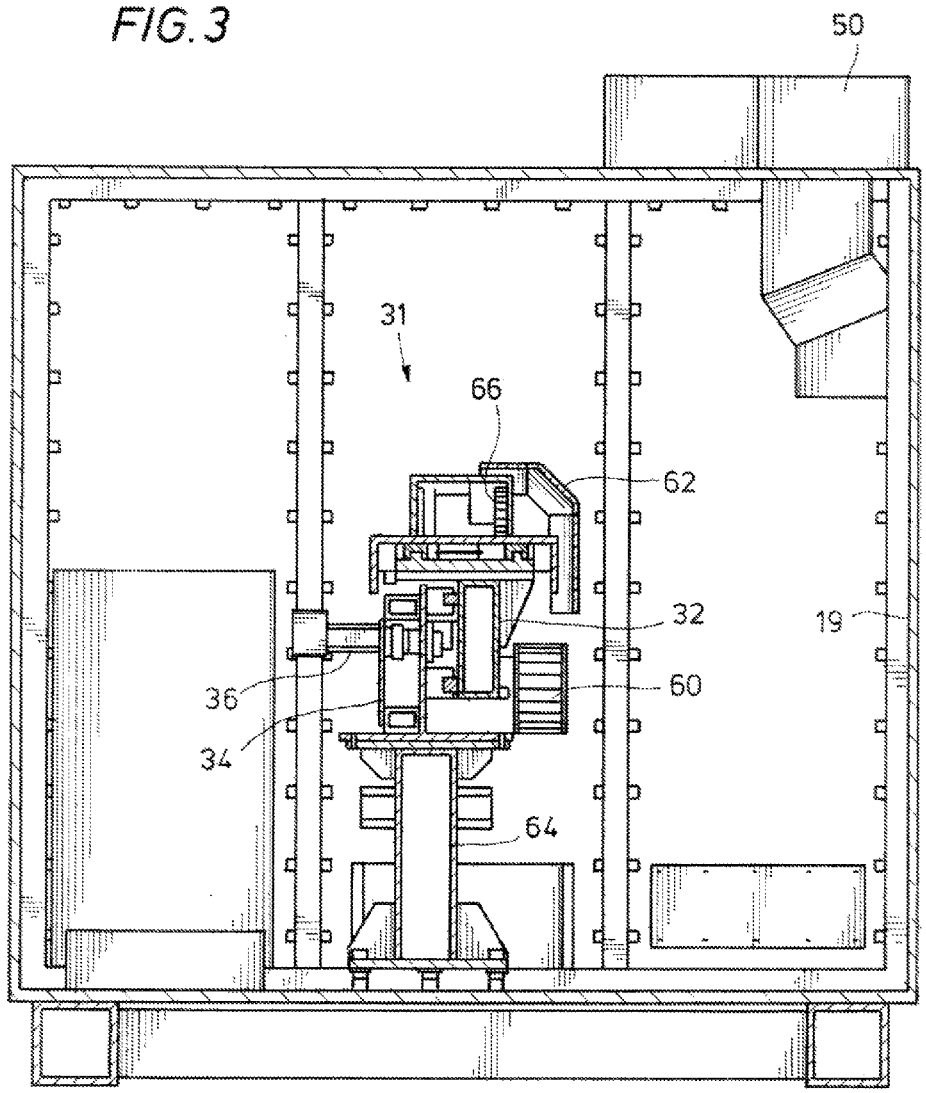
FIG. 3 is an axial sectional view of the cabinet of FIG. 2 and taken along lines 3-3.

FIG. 3 shows an example of the cabinet 19 in a sectional view and taken along lines 3-3 of FIG. 2. This view which is taken along the axial portion of manipulator system 31 shows one example of a wiring track 60; which has cross members for organizing the control and power wires needed for use in the scan system 18 and as the manipulator arm 32 axially moves with respect to manipulator base 34. Wiring track 60 maintains the wires in a designated location and position with use of wiring track 60 during operation of the manipulator system 31. Further in the example of FIG. 3 is a shroud 62 shown mounted on an upper end of manipulator system 31 and which covers a portion of the upper end and shields components within the manipulator system 31. Manipulator base 34 (and thus manipulator arm 32) is supported on a vertical mounting pedestal 64, which has a generally rectangular cross section along its axis, and has a lower end mounted on the floor of cabinet 19. Shown housed within shroud 62 is a wiring bus 66 which extends axially along the manipulator assembly.

Figure 4:
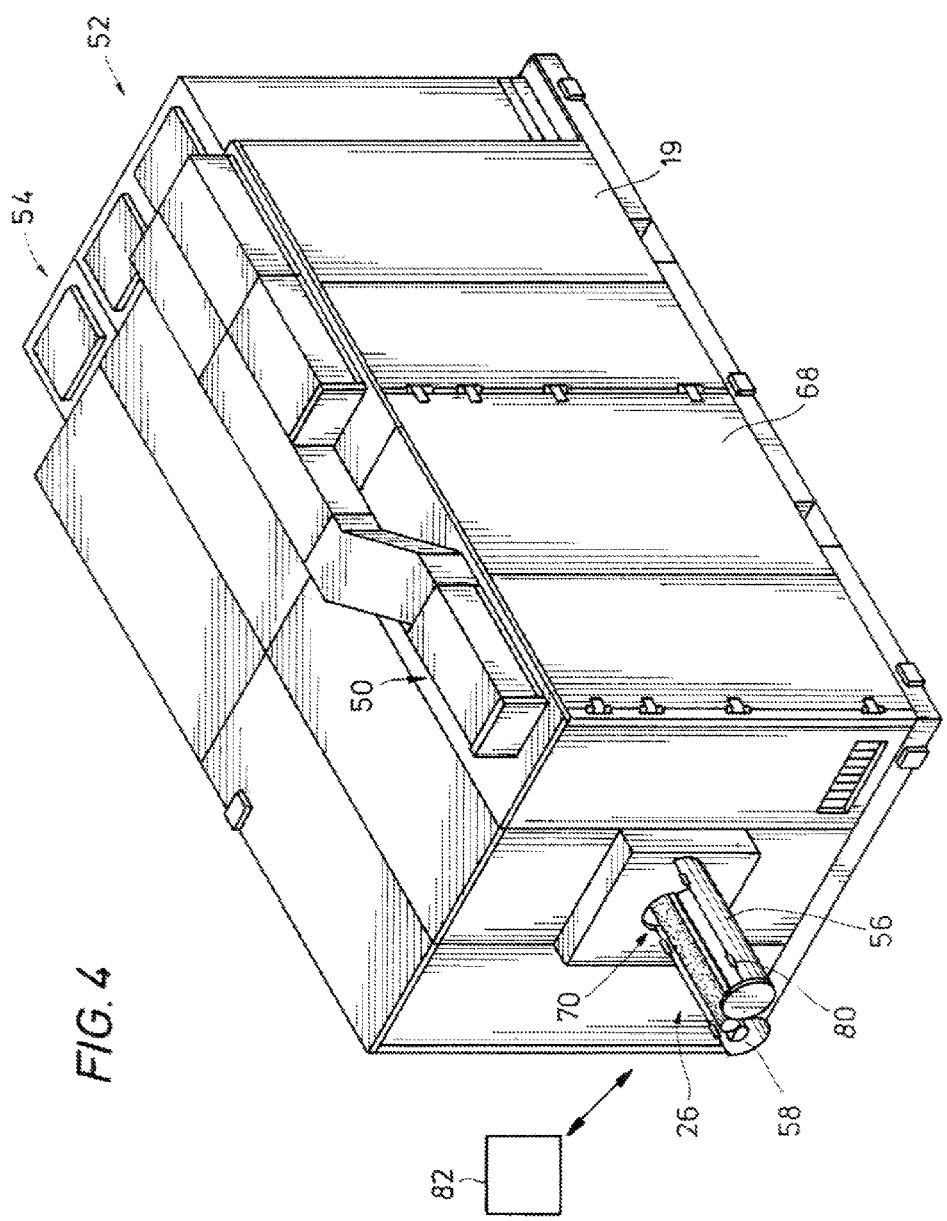
FIG. 4 is a perspective view of the cabinet of FIG. 2.

FIG. 4 provides in perspective view of one example of the cabinet 19 and having hinged panel 68 along its outer surface. As indicated above, the structure of cabinet 19 is in compliance with 21 C.F.R. 1020.40. Thus proper protective shielding and interlocking is provided in the panel 68 and along the hinged interface. An additional safety feature is a door assembly 70 which includes a barrier (not shown) that slides axially across the opening shown at the base of the loading assembly 26 and in a forward wall of cabinet 19. The barrier thus provides a radiation shield from the inside to the outside of cabinet 19 while still allowing core sample loading in compliance with 21 C.F.R. § 1020.40.

Figure 5:
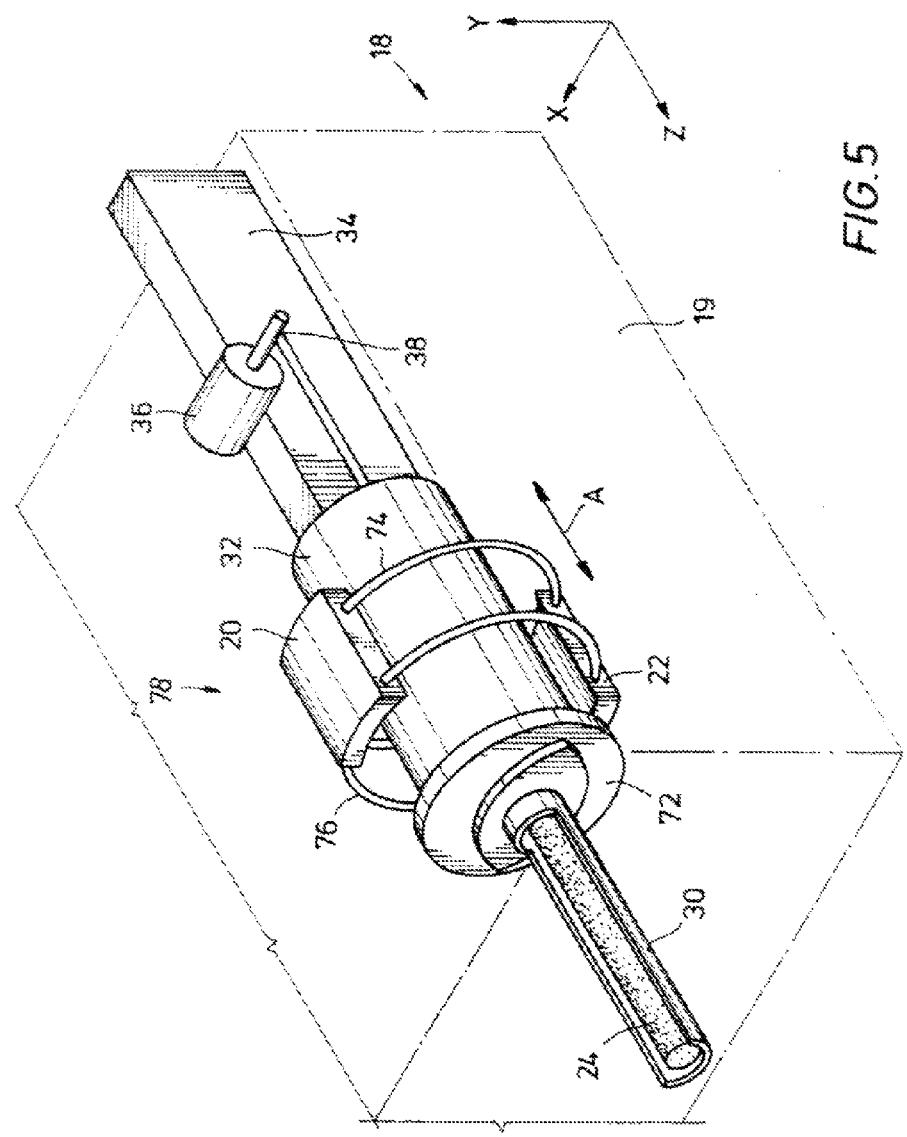
FIG. 5 is a perspective view of the cabinet of FIG. 2 in partial phantom view and an example scanning unit in the cabinet.

An example of the manipulator assembly within cabinet 19 is illustrated in perspective view in FIG. 5, and where cabinet 19 is shown in a partial phantom view. In this embodiment, a rearward end of manipulator base 34 is supported on a rearward end of cabinet 19; manipulator base 34 extends axially away from the rearward wall of cabinet 19 with the manipulator arm 32 axially sliding on manipulator base 34. Motor 36 is shown oriented generally perpendicular to an axis of manipulator arm 32 and manipulator base 34, and couples to manipulator arm 32 by shaft 38. Further illustrated is how the core carrier 30 couples to a mounting plate 72; where mounting plate 72 is a generally circular and planar member that mounts on a forward end of manipulator arm 32. In one embodiment, this member along with an extended tunnel provides the seal that inhibits excessive air flow during the loading process.

Axial movement, as shown by the double headed arrow A, of core sample 24 is accomplished via motor 36. X, Y, and Z axes are illustrated to define an example coordinate system for the purposes of reference herein. While not limited to this coordinate system, the axes depict axial movement of any object, such as the core sample 24, to be along the Z axis, vertical movement to be along the Y axis, and lateral movement to be along the X axis. As indicated above, operation of motor 36 can move core sample 24 along all of these axes. Further shown in FIG. 5 are curved supports 74, 76 that circumscribe manipulator arm 32 and provide a mounting surface for scan source 20 and scan receiver 22. The combination of the support 74, 76 define a gantry 78 that when rotated puts the scan source 20 and scan receiver 22 at an orbiting rotation around the core sample 24 and provides the scanning capabilities of the scan system 18. As indicated above, the air replacement capabilities provided with cabinet 19 maintains a substantially constant temperature across the gantry 78.

Referring back to FIG. 4, an interlock connector 80 is shown provided on the loading cover 56 and loading basin 58. The interlock connectors 80 thus may recognize when the cover 56 is in the open position of FIG. 4 and in combination with controller 82 may prevent operation of the manipulator system 31. However, the control system associated with the scan system 18 that allows for motion of the manipulator system 31 when the cover 56 is in the closed position and interlock connectors 80 are adjacent one another.

Referring now back to FIG. 1, schematically illustrated is an example of a core handling system 84 disposed within the handling trailer 14. In the example shown, core handling system 84 handles core samples 24 shown arranged in a staging area 85 set adjacent handling trailer 14. Included with the core handling system 84 is an articulated arm 86, which selectively extends outward from within the handling trailer 14 to grasp one of the core samples 24 in the staging area 85. Arm 86 can also then dispose the core sample 24 into the loading assembly 26 for scanning the core sample 24 in the scan system 18; and remove the core sample 24 from the loading assembly 26 after scanning is complete. Further in the illustrated example, an end effector 88 having automated grappling elements 89 grasps and holds the core sample 24 during handling. In the embodiment shown, grappling elements 89 are elongate finger like elements that may or may not be articulated, and which grapple the core sample 24 by positioning elements 89 on opposite sides of the core sample 24 and then are moved towards one another to apply a grappling force onto the core sample 24. An optional scanner 90 is provided with the end effector 88 for registering information about the core sample 24. In an alternate embodiment, an identification tag 92 is shown on the core samples 24 for obtaining information about the core sample 24 that can be used during handling of the core sample 24. For example, the information on the identification tag 92 can include a core identifier, vertical orientation of the core sample 24, and slab side orientation of the core sample 24. In an example, slab side orientation of the core sample 24 defines the azimuthal orientation of the core sample 24 when it was obtained from the formation (not shown). The scanner 90 can be optical radar, infrared, ultrasound, or combinations thereof.

An optional controller 94 for controlling and/or monitoring operation of the core handling system 84 is shown in communication with the core handling system 84. In the example shown, controller 94 communicates with core handling system 84 via communication means 96 and communicates with scan system 18 via communication means 98. Communication means 96, 98 can be solid, such as signal lines and/or printed circuit boards, or can be wireless, such electromagnetic waves, radio waves, infrared waves and the like. In a non-limiting example of operation, controller 94 provides operational commands to core handling system 84 and/or scan system 18 to oversee handling of the core samples 24 between the staging area 85 and scan system 18. Examples exist where controller 94 receives communication from the core handling system 84 and/or scan system 18, where the communication can include information from the identification tag 92. Thus during scanning, information from the identification tag 92 can be integrated with information obtained during the scan so that orientation, location in the formation, and slab side orientation of the core sample 24. In an embodiment, core handling system 84 can be commanded to seek out and retrieve a specific one of the core samples 24, where the command can be initiated by an operator (not shown), or via controller 94. An advantage of this feature is when core samples 24 that were obtained from adjacent locations in the wellbore are to be scanned sequentially. Alternatively, the arm 86 can be equipped with a marking instrument (not shown) for marking or otherwise identifying a specific location on the core sample 24 for further analysis.

Figure 6:
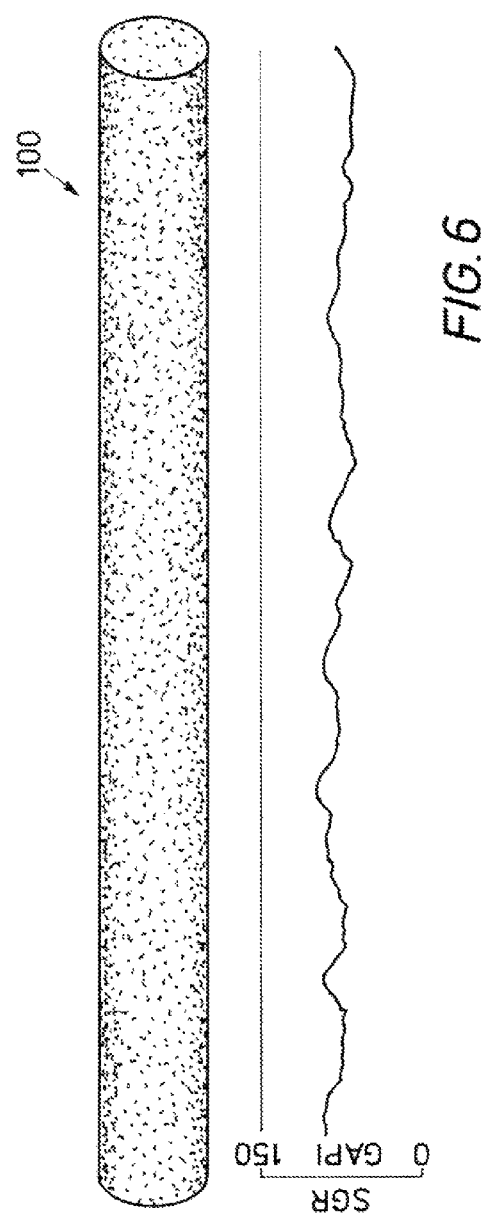
FIG. 6 is a perspective view of an example of an image of a core sample.

Using the information from the identification tag 92 about the core sample 24 in conjunction with the information obtained while scanning, a scan image 100 (FIG. 6) can be generated. Moreover, the scan image 100 can be correlated with other known data known about the core sample 24 so that visually observing the scan image 100 can yield more information about the formation from where the core sample 24 was extracted than would be available without the step of correlating with the other known data. An additional step of analysis possible by correlating scan data with information about the core sample 24 is radial indexing.

An advantage exists by maintaining knowledge of the orientation of the core sample 24. This enables proper correlation of the scanned information to the depth, orientation, gamma, and slab side orientation of the core sample 24. Thus meaningful information can be obtained about the formation from where the core sample 24 was taken. Based on the results of the scan, the core handling system 84 can strategically position the particular core sample 24 at a designated location in the work 42, or other area, so that additional analysis of the particular core sample 24 can be performed. Additional functions performed by the scanner 90 include inspecting each core sample 24 for contamination and integrity of the core sample 24.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. For example, in an embodiment, mounting and shock absorption hardware is provided for securing the components in the core analysis system 10 to maintain their integrity and alignment during transportation in the trailers. The gantry can include reinforced mounting for rotating elements and added adhesive for board mounted components, e.g. integrated circuitry, resistors, capacitors, and the like. A transport locking mechanism can be used to prevent sliding door movement when power is removed, and a locking mechanism can be used on all threaded fasteners. All circuit boards can be mechanically secured to reduce vibration and remove gravity loading on connectors. Relays can be secured to mounting sockets, and expansion loops can be added in all cables and hoses and secured to cabinet walls. High voltage cables can be cushioned, and service door fastening can be added to prevent load on interlock closure. Cooling tan mounting can be reinforced and cooler unit can be secured for shipment. Also, transformer can be set near high voltage generator by mounting to the floor of the cabinet. An advantage of this is a scanned image of the core sample 24 can be produced at a resolution of up to 200 microns. These and other similar modifications will readily suggest themselves to those skilled in the art, and are intended to be encompassed within the spirit of the present invention disclosed herein and the scope of the appended claims.

What is claimed is:

1. A method of analyzing a core sample by subjecting the core sample to radiation emitted by a scan source, the method comprising:
   enclosing the scan source and core sample in a cabinet to contain radiation emitted during the core sample analysis, the core sample inserted into the cabinet via a loading assembly that axially translates the core sample from a position outside of the cabinet into the cabinet, the scan source being movable within the cabinet, in an axial direction relative to the core sample, the axial direction being in the same plane as the movement of the core sample into the cabinet, wherein a core handling system installs the core sample into the loading assembly, the handling system arranged outside of the cabinet;
   providing information on the core sample;
   retrieving the information provided on the core sample; and
   handling the core sample based on the step of retrieving the information provided on the core sample.

2. The method of claim 1, further comprising imaging the core sample.

3. The method of claim 2, wherein the core sample is maintained in a designated orientation during the step of imaging based on the information retrieved from the core sample.

4. The method of claim 2, further comprising correlating the information retrieved from the core sample with an image obtained by imaging the core sample.

5. The method of claim 2, further comprising moving the core sample to a designated location based on information obtained from the step of imaging the core sample.

6. The method of claim 5, further comprising further analyzing the core sample at the designated location with a device selected from the group consisting of a spectroscope, a laser, and combinations thereof.

7. The method of claim 6, further comprising disposing the core sample at a staging area, and wherein the step of handling the core sample comprises moving the core sample from the staging area to the core sample imaging device with the core handling system.

8. The method of claim 1, wherein the information provided on the core sample comprises the data that is selected from the group consisting of a core identifier, vertical orientation of the core sample, slab side orientation of the core sample, and combinations thereof.

9. The method of claim 1, wherein the step of handling the core sample comprises using the core handling system with an articulated arm to insert the core sample into a core sample imaging device.

10. A method of analyzing a core sample by subjecting the core sample to radiation emitted by a scan source, the method comprising:
    enclosing the scan source and core sample in a cabinet to contain radiation emitted during the core sample analysis, the core sample inserted into the cabinet via a loading assembly that axially translates the core sample from a position outside of the cabinet into the cabinet, the scan source being movable within the cabinet, in an axial direction relative to the core sample, wherein a core handling system installs the core sample into the loading assembly, the handling system arranged outside of the cabinet and comprising an articulated arm to insert the core sample into the loading assembly;
    providing information on the core sample;
    retrieving the information provided on the core sample;
    handling the core sample based on the step of retrieving the information provided on the core sample;
    imaging the core sample while maintaining the core sample in a designated orientation based on the information retrieve from the core sample, the scan source moving during the imaging; and
    correlating the information retrieved from the core sample with an image obtained by the imaging the core sample.

11. The method of claim 10, further comprising moving the core sample to a designated location based on information obtained from the step of imaging the core sample.

12. The method of claim 10, wherein the step of handling the core sample comprises using the core handling system to insert the core sample into a core sample imaging device.

13. The method of claim 10, further comprising disposing the core sample at a staging area, and wherein the step of handling the core sample comprises moving the core sample from the staging area to the core sample imaging device with the core handling system.

14. A system for analyzing a core sample by subjecting the core sample to radiation emitted by a scan source, the system comprising:
    a mobile enclosure that seals an area around the scan source and the core sample to contain radiation emitted during analysis of the core sample, the scan source being movable in an axial direction relative to the core sample within a cabinet positioned within the mobile enclosure;
    a core sample imaging device within the mobile enclosure;
    a loading assembly that selectively receives the core sample and axially translates the core sample into the cabinet in the same plane as the axial direction; and
    a core handling system that selectively handles the core sample between the loading assembly and a staging area, is arranged outside of the cabinet, and installs the core sample into the loading assembly.

15. The system of claim 14, wherein the core handling system comprises having an articulated arm for manipulating the core sample.

16. The system of claim 14, wherein the core handling system comprises a scanner that scan information provided on the core sample to identify the core sample.

17. The system of claim 14, wherein the core handling system maintains the core sample in a designated orientation based on information provided on the core sample.

18. The system of claim 14, wherein information about the core samples is listed on identification tags provided on the core samples.

19. The system of claim 18, wherein the information comprises the data that is selected from the group consisting of a core identifier, vertical orientation of the core sample, slab side orientation of the core sample, and combinations thereof.

20. The system of claim 14, further comprising a controller in communication with the core sample imaging device and the core handling system.

* * * * *